United States Patent
Tolley et al.

(10) Patent No.: US 8,308,740 B2
(45) Date of Patent: Nov. 13, 2012

(54) NEEDLE STABILIZER

(76) Inventors: Kristin Ann Tolley, Pittsford, NY (US); Mary-Catherine Marshall, Pittsford, NY (US)

( * ) Notice: Subject to any disclaimer, the term of this patent is extended or adjusted under 35 U.S.C. 154(b) by 1620 days.

(21) Appl. No.: 11/422,110

(22) Filed: Jun. 5, 2006

(65) Prior Publication Data

US 2008/0006551 A1    Jan. 10, 2008

(51) Int. Cl.
*A61B 19/00* (2006.01)
(52) U.S. Cl. .................. 606/130; 604/116; 604/117
(58) Field of Classification Search .................. 606/160, 606/130, 108, 167, 189; 604/180, 174, 177, 604/116, 117, 164.01, 167.06
See application file for complete search history.

(56) References Cited

U.S. PATENT DOCUMENTS

| | | | |
|---|---|---|---|
| 3,021,842 A * | 2/1962 | Flood | 604/175 |
| 3,487,837 A * | 1/1970 | Petersen | 604/180 |
| 3,900,026 A | 8/1975 | Wagner | |
| 4,392,854 A * | 7/1983 | Ibach | 604/174 |
| 4,516,968 A * | 5/1985 | Marshall et al. | 604/174 |
| 4,519,793 A * | 5/1985 | Galindo | 604/180 |
| 4,675,006 A * | 6/1987 | Hrushesky | 604/180 |
| 4,883,053 A | 11/1989 | Simon | |
| 4,985,019 A * | 1/1991 | Michelson | 604/180 |
| 4,988,341 A * | 1/1991 | Columbus et al. | 604/306 |
| 5,074,847 A * | 12/1991 | Greenwell et al. | 604/174 |
| 5,201,742 A | 4/1993 | Hasson | |
| 5,728,071 A * | 3/1998 | Watson et al. | 604/180 |
| 5,776,106 A | 7/1998 | Matyas | |
| 5,943,719 A * | 8/1999 | Feldman et al. | 606/130 |
| 6,159,221 A * | 12/2000 | Chakeres | 606/130 |
| 6,524,297 B1 | 2/2003 | Newman | |
| 6,533,794 B2 * | 3/2003 | Chakeres | 606/130 |
| 6,921,406 B1 * | 7/2005 | Chakeres | 606/130 |
| 7,785,302 B2 * | 8/2010 | Powers | 604/288.02 |
| 2004/0199129 A1 * | 10/2004 | DiMatteo | 604/288.02 |
| 2004/0220588 A1 | 11/2004 | Kermode et al. | |
| 2004/0260312 A1 | 12/2004 | Magnusson et al. | |

* cited by examiner

*Primary Examiner* — Gary Jackson
*Assistant Examiner* — Katrina Stransky
(74) *Attorney, Agent, or Firm* — Louis S. Horvath

(57) ABSTRACT

A stabilizing apparatus for stabilizing the position of a needle when penetrating the skin of a patient, the apparatus has a frame structure with a base for placement against the skin in the vicinity of an intended needle entry point. A flexible diaphragm is supported by the frame structure and is spaced apart from the base of the frame structure to be disposed at a position away from the skin. The flexible diaphragm is configured to releasably grip the shaft of the needle at a distance from the needle entry point.

11 Claims, 6 Drawing Sheets

NEEDLE STABILIZER

FIELD OF THE INVENTION

This invention generally relates to medical apparatus for surgical instrument positioning and more particularly relates to an apparatus and method for stabilizing the position of a needle or other device inserted into a patient during diagnostic testing or treatment.

BACKGROUND OF THE INVENTION

Computerized Axial Tomography apparatus, commonly referred to as CAT or CT scanner devices, have proven to be of particular value in detection of cancer and other life-threatening conditions. Images obtained using CT scanners can help the diagnosing physician to visualize and localize an area of pathological tissue. However, in many cases, a biopsy of this tissue is then needed in order to provide an accurate diagnosis. Tissue samples are commonly obtained by puncturing the skin of the patient with a biopsy needle, guiding the needle to the site of the suspected tumor, and withdrawing a sample of the tissue.

Even with the help of a CT scan image that identifies the location of pathological tissue, however, it can be difficult to obtain a tissue sample from the suspected area. Lesions can be quite small and it can be extremely difficult to guide the biopsy needle to the proper penetration depth and angle needed. In response to this difficulty, one useful technique for obtaining a tissue sample from a suspected lesion is the CT-guided biopsy. In this technique, CT scanning or CT fluoroscopy is used as feedback to help position a biopsy needle to the proper location for extraction of a tissue sample.

Even though it uses CT imaging capabilities for biopsy needle positioning, CT-guided biopsy can be an iterative process. The biopsy needle is inserted to the approximate location, then a localized CT scan or a CT fluoroscopic image of this area is obtained as feedback on needle position, angle, and depth. The image that has been obtained is then used as a guide to readjust and correct needle position. With each iteration, the biopsy needle may be repositioned in the patient. Even with local anesthetics, this iterative procedure can be painful and uncomfortable for the patient as well as costly and time-consuming. Movement of the patient can inadvertently cause the needle to be shifted in position, requiring repetition of the sampling process. Moreover, each repeated scan increases the radiation risks to the patient and, particularly with CT fluoroscopy, to the radiologist, nurse, or CT operator.

In an effort to alleviate the positioning problem and provide stabilizing means for the biopsy needle, some types of CT devices have been outfitted with positioning components. However, these solutions have not satisfactorily resolved the positioning problem and, in a large number of cases, go unused. Alternately, there have been a number of solutions proposed for devices that assist in needle placement and positioning. A few examples of needle stabilization apparatus are the following:

- U.S. Patent Application Publication No. 2004/0260312 entitled "Guide for a Medical Device" by Magnusson et al. describes a needle guide supported by a retainer for maintaining a needle or other medical instrument at a suitable position and angle.
- U.S. Pat. No. 4,733,661 entitled "Guidance Device for C.T. Guided Drainage and Biopsy Procedures" to Palestrant describes a device for needle positioning that includes a support arm provided in a protractor-like arrangement and equipped with various devices to aid in proper needle orientation.
- U.S. Pat. No. 4,883,053 entitled "Self-Supporting Angulator Device for Precise Percutaneous Insertion of a Needle or Other Object" to Simon describes a collapsible device that can be placed against the patient, the device having hinged sections that cooperate with a bracket to obtain the desired angular orientation of a needle.
- U.S. Pat. No. 5,354,283 entitled "Trocar Retention Apparatus" to Bark et al. describes a stabilizing apparatus for this type of inserted instrument, using a base that supports a rotatable spheroid element for allowing the adjustment of angular movement of the instrument.

A number of patent disclosures describe needle positioning devices for various types of medical procedures, where the devices use some type of protractor mechanism to adjust a needle holder to a specific angle over some range of angles. For example: U.S. Pat. No. 4,841,967 entitled "Positioning Device for Percutaneous Needle Insertion" to Chang et al.; U.S. Pat. No. 5,941,889 entitled "Multiple Angle Disposable Needle Guide System" to Cermak; and U.S. Pat. No. 5,201,742 entitled "Support Jig for a Surgical Instrument" to Hasson show this type of arrangement.

Each of these solutions, however, has its drawbacks. Many of the devices described in the above-cited patent literature are mechanically complex, making them difficult to use and to adapt to different areas of the body. For example, a number of these conventional devices employ spherical ball-and-socket mechanisms or have protractor arms for obtaining precision angular adjustments. Only a small number of these proposed solutions could be provided inexpensively as a sterilized, disposable item.

Considering the complexity of the CT-guided biopsy, it is well recognized that a device for stabilizing needle position should be easy to use, allowing the medical team to concentrate on safely and expeditiously performing this task. Since the CT-guided biopsy typically involves the iterative process described earlier, a needle stabilizing apparatus should allow good visibility of the skin area and should allow ease of readjustment, which are not features shared by many of the devices cited above. A needle stabilizing device should be as compact as possible and should be readily adaptable for use on different areas of the skin.

SUMMARY OF THE INVENTION

It is an object of the present invention to advance the art of surgical instrument positioning. With this object in mind, the present invention provides a stabilizing apparatus for stabilizing the position of a needle when penetrating the skin of a patient, the apparatus comprising:

a) a frame structure having a base for placement against the skin in the vicinity of an intended needle entry point; and b) a flexible diaphragm supported by the frame structure and spaced apart from the base of the frame structure to be disposed at a position away from the skin, wherein the flexible diaphragm is configured to releasably grip the shaft of the needle at a distance from the needle entry point.

It is a feature of the present invention that it uses a flexible diaphragm, raised above the surface of the skin, to allow pivoting action of an inserted needle or other surgical instrument.

It is an advantage of the present invention that it can be fabricated as a small, lightweight, low-cost, disposable item.

These and other objects, features, and advantages of the present invention will become apparent to those skilled in the art upon a reading of the following detailed description when taken in conjunction with the drawings wherein there is shown and described an illustrative embodiment of the invention.

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

As used in the present disclosure, the general term "needle" or "puncturing instrument" encompasses any of a variety of devices used to penetrate into or puncture the skin of a patient in various surgical procedures. The term needle or puncturing instrument would include, but not be limited to, such devices as biopsy needles, catheters including drainage catheters, hypodermic needles, other types of conduits inserted beneath the skin surface, and the like.

The term "frame" is used with its conventional meaning to describe an open support structure for an object. The apparatus of the present invention employs a frame structure for the advantage of visibility of a supported needle.

Figure 1:
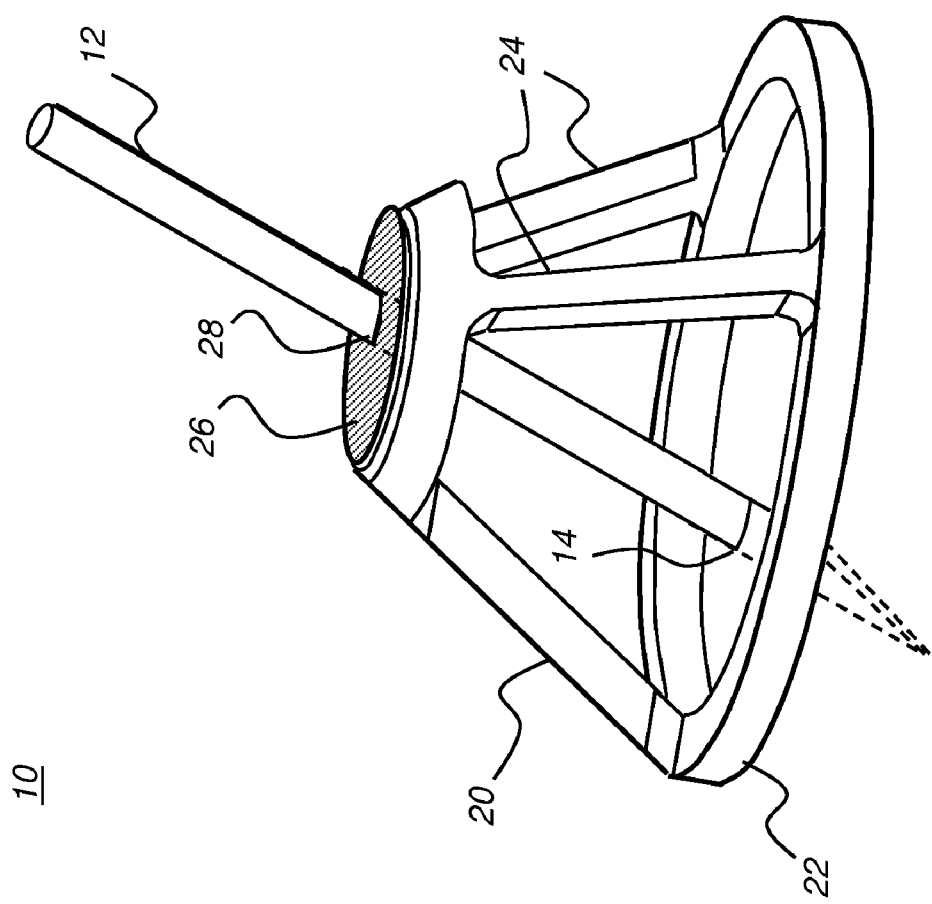
FIG. 1 is a perspective view showing a needle stabilizer apparatus of the present invention.

Referring to the perspective view of FIG. 1, there is shown a stabilizer 10 for a needle or other type of puncturing instrument, according to the present invention. FIG. 1 shows how stabilizer 10 is capable of supporting a needle 12 that penetrates the skin of a patient at a needle entry point 14. Stabilizer 10 has a frame 20 with a base 22 that seats stabilizer 10 against the patient in the vicinity of needle entry point 14. In the particular embodiment of FIG. 1, there are a number of extending members 24 of frame 20 that extend upward from base 22. Frame 20 supports a flexible diaphragm 26 that is apertured for needle 12, provided with an aperture 28 in the embodiment of FIG. 1. Diaphragm 26 cradles needle 12 securely in position so that repositioning of the patient is less likely to disturb a diagnostic or treatment procedure. In the embodiment shown, needle entry point 14 lies within the area bounded by base 22. This provides a stable arrangement for holding needle 12 in position.

Figure 2:
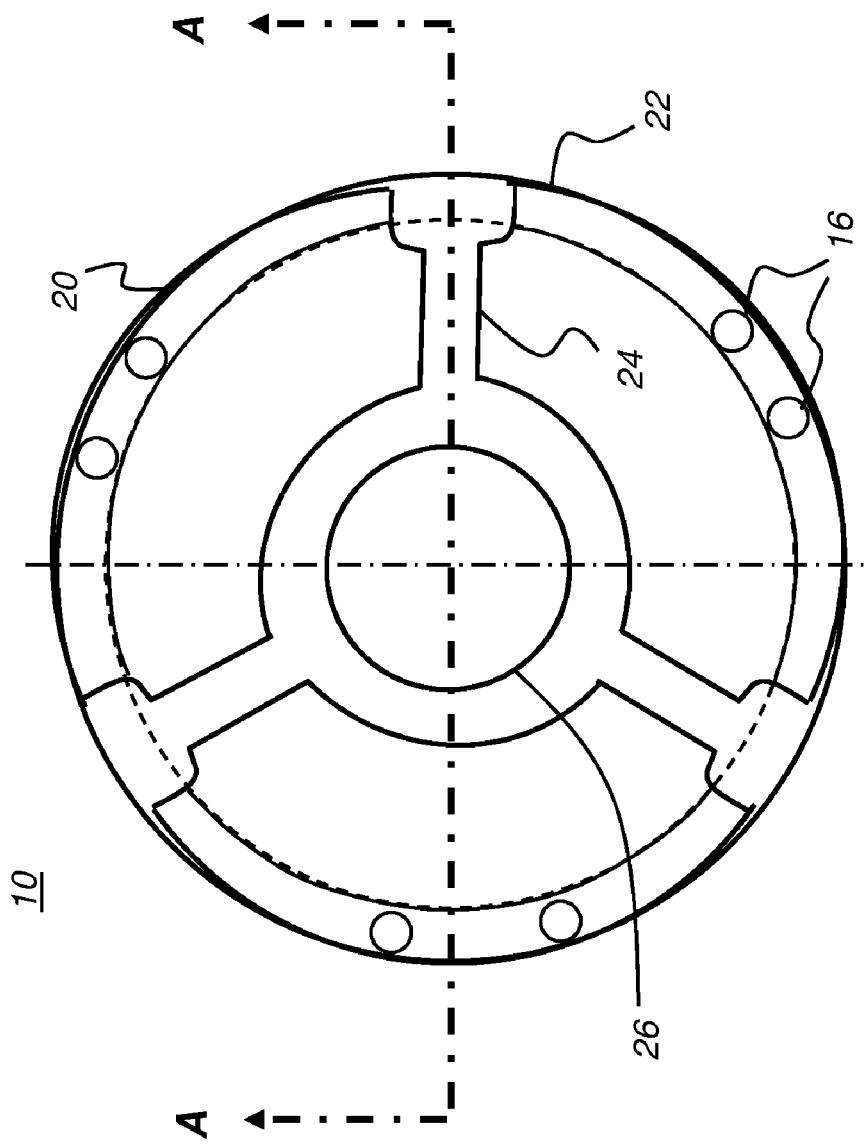
FIG. 2 is a top view of the stabilizer apparatus in one embodiment.
Figure 3:
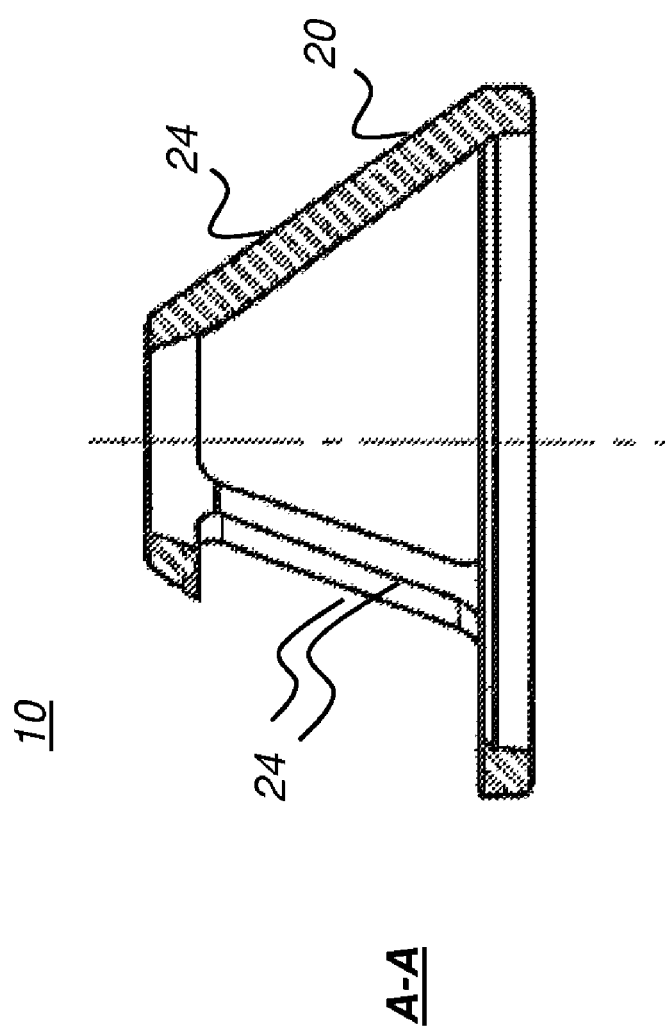
FIG. 3 is a side view of the stabilizer apparatus, taken from view A-A in FIG. 2.

The top view of FIG. 2 shows the central position of diaphragm 26 relative to frame 20 in one embodiment. As shown here and in FIG. 3, which is taken along line A-A from FIG. 2, frame 20 provides a tripod with three extending members 24. Significantly, this arrangement of frame 20 as an open frame structure provides a considerable portion of visible "window" around needle entry point 14, as suggested in each of FIGS. 1, 2, and 3. For the user, there is little or no obstruction of view caused by the supporting structure. The skin area circumscribed by base 22 is not obstructed, allowing substantially full visibility for locating and manipulating puncturing instrument position into the intended entry point. This high visibility at the point of needle 12 entry is particularly useful to the physician or other medical professional and simplifies the job of positioning needle 12 or other device at the proper site and at the correct angle for positioning the needle tip. It can be observed that this high visibility design is unlike that of a number of conventional needle support and stabilizing components that are conventionally used, such as those cited earlier in the Background section, where the puncture point may not be clearly visible or where it can only be viewed from a restricted range of angles.

To simplify use of stabilizer 10, base 22 can be conditioned or treated in some way to foster adhesion to the patient's skin. Adhesion can be obtained in a number of ways, such as by applying an adhesive substance to the contact surface of base 22. In one embodiment, the contact surface of base 22 is provided with an adhesive and covered temporarily, at manufacture, by a protective pad (not shown) that is removed at the time of use to expose the adhesive surface when stabilizer 10 is first placed against the patient. Alternately, base 22 could be adhered to the patient's skin using an adhesive member or membrane such as an adhesive tape of the type conventionally used for bandage dressings. This could be advantageous, for example, when stabilizer 10 must be positioned over some portion of the skin surface that does not provide a sufficiently flat surface area for directly adhering base 22.

Suction could alternately be used as an adhesion mechanism for base 22. Base 22 would be featured with one or more suction cups in one embodiment. Suction could alternately be used in combination with adhesive substances.

Figure 4:
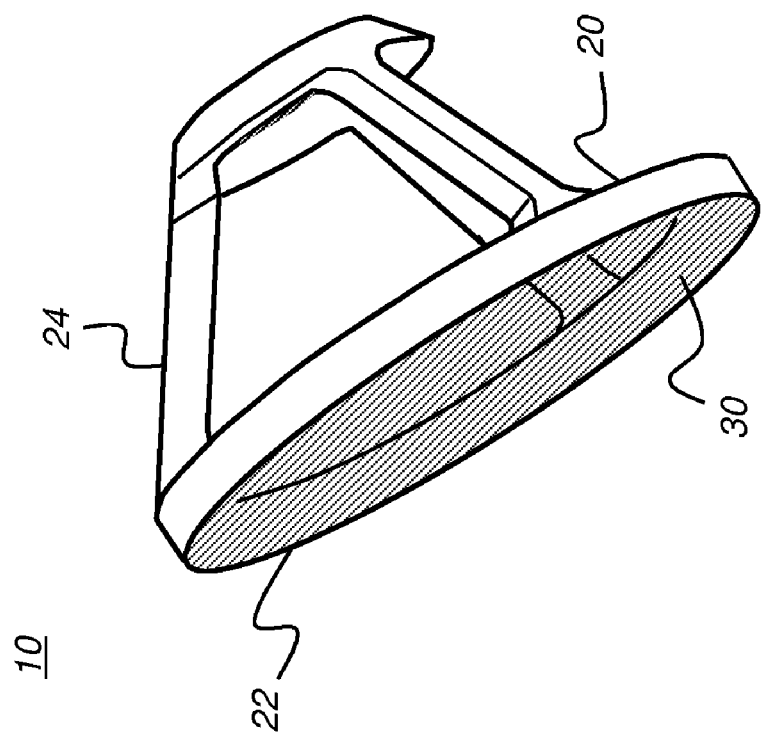
FIG. 4 is a perspective view of a needle stabilizer, taken from the base.

In the embodiment of FIG. 4, base 22 includes a membrane or film 30 or other dressing material that is placed against the skin. Some or all of film 30 may be adhesive. To allow good visibility of needle entry point 14, film 30 is preferably transparent or substantially transparent. In one embodiment, film 30 is a transparent dressing, such as Tegaderm™ transparent dressing, a product of 3M, Inc., St. Paul, Minn. Film 30 could also be an injection patch such as is described in U.S. Pat. No. 5,728,071 to Watson et al. or a sterilizing dressing such as that described in U.S. Pat. No. 4,988,341 to Columbus et al.

Figure 5:
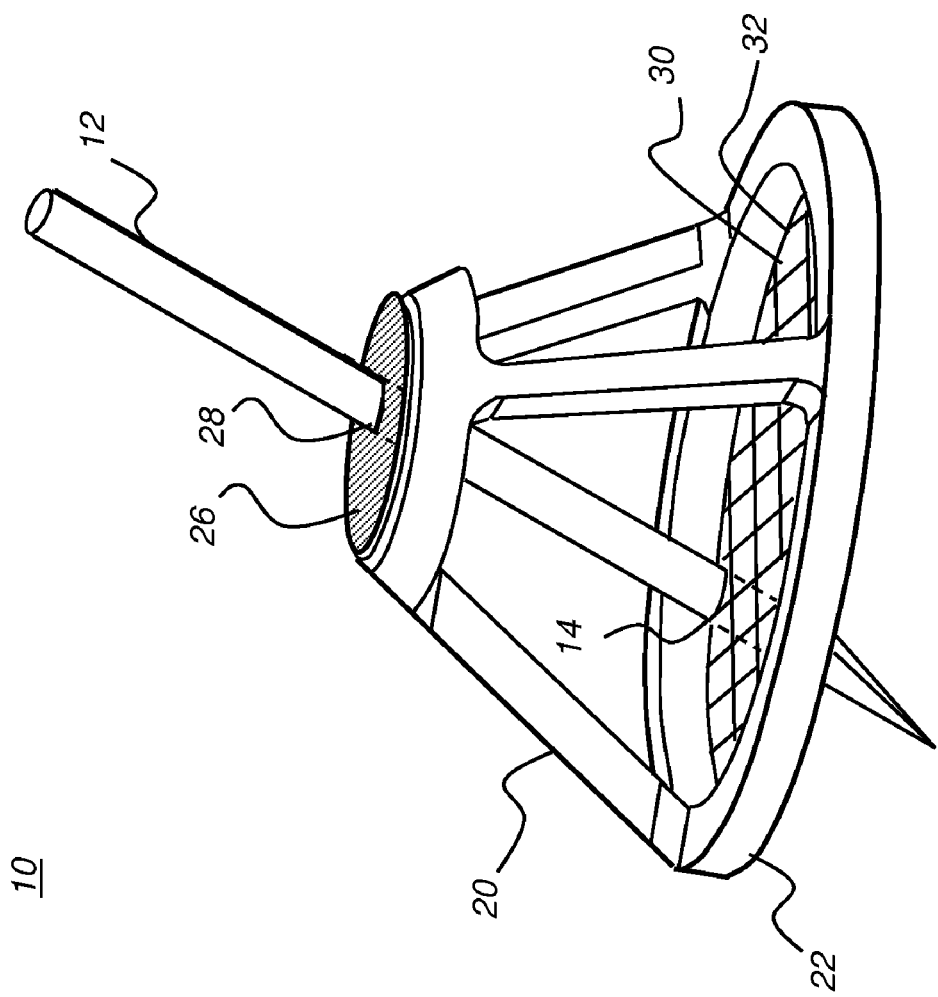
FIG. 5 is a perspective view showing a needle stabilizer apparatus having a patterned membrane to assist in needle positioning.

FIG. 5 shows another embodiment, in which film 30 on base 22 is provided with a grid or other pattern 32. The use of optional pattern 32 can facilitate locating the intended entry point 14 for insertion of needle 12 or other type of surgical instrument.

As was noted earlier, frame 20 is designed to maximize the visibility of the puncture area in the vicinity of the entry point of needle 12. In embodiments shown in FIGS. 1-5, frame 20 is skeletal, having only as much structure as is needed to support diaphragm 26 in a position such that it is spaced apart from the skin surface and to support the added burden of needle 12 or other puncturing instrument inserted into aperture 28. In other embodiments, frame 20 could include additional structure and could include transparent sections for enhancing entry point visibility as well as including opaque sections. Frame 20 can be fabricated from any of a number of materials, with plastics offering particular advantages for cost and ease of use. Plastic components would also be easy to package and to provide in sterilized form. In one embodiment, frame 20 of stabilizer 10 is formed from an injection molded thermoplastic, such as acrylic, for example.

Diaphragm 26 is preferably formed from a flexible material, such as a rubberized plastic or an elastomer such as neoprene. The material used for diaphragm 26 should be flexible, but within a range of flexibility suited to its purpose, generally spanning the overall flexibility range exhibited by rubber or elastomer materials. Diaphragm 26 is typically apertured, that is, having aperture 28 already formed, to releasably grip the shaft of needle 12 or other surgical instrument following insertion. Aperture 28 can be a perforation that is pre-formed in diaphragm 26 when the part is molded or otherwise fabricated. Optionally, aperture 28 could be a molded depression that leaves a thin area for piercing with needle 12 when it is inserted by the doctor or other staff member. In yet other embodiments, no aperture 28 is provided; insertion of needle 12 pierces diaphragm 26 and forms its own aperture 28 directly. Diaphragm 26 can be separately fabricated from frame 20 and glued, force-fitted, or otherwise attached in position. Optionally, one-piece fabrication of stabilizer 10 is possible, so that diaphragm 26 and base 20 are formed from the same piece of material.

It can be appreciated that stabilizer 10 of the present invention offers a number of significant advantages over earlier solutions for needle positioning and stabilization. Unlike complex apparatus that may be provided as part of the diagnostic imaging device, stabilizer 10 is inexpensive and is simple to use. Because exact positioning must often be obtained through an iterative process, the relative ease of use of stabilizer 10 makes it particularly useful in this environment and advantaged over other solutions for CT-assisted biopsy applications. The use of stabilizer 10 can result in reduced time, lower cost, and reduced dosimetric exposure risk, both for patients and for medical personnel.

Stabilizer 10 can be disposable and can be made from materials that are readily sterilized, either by the manufacturer or at the time of use. Stabilizer 10 can be taped to the patient or adhesively attached to the skin of the patient in a number of ways, including self-adhesive embodiments with or without an attached film 30. Various types of film 30 could be provided as part of base 22, including wound bandaging and skin or needle conditioning materials. Stabilizer 10 can be provided in a number of sizes, based on patient age and size and on the size and use requirements of needle 12 or of other puncturing instrument that is used.

Figure 6:
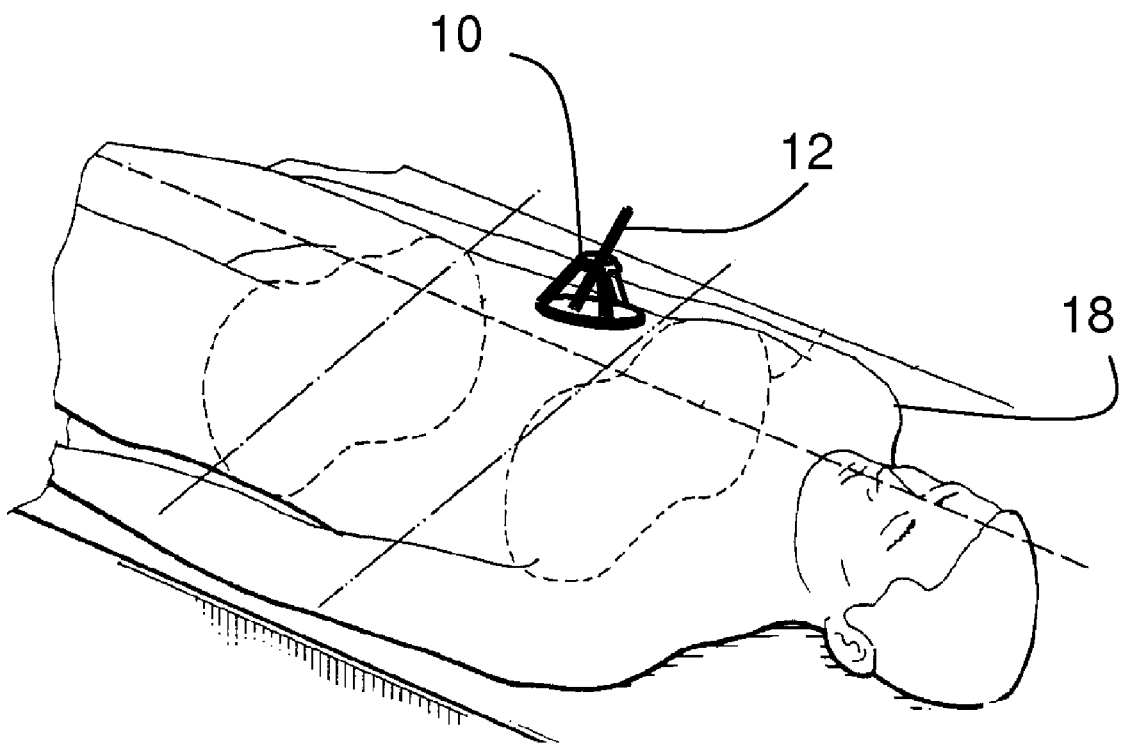
FIG. 6 is a perspective view showing the use of the needle stabilizer of the present invention in one application.

By way of illustration, the perspective view of FIG. 6 shows stabilizer 10 as it may be used on the chest of a patient 18, such as for a fluoroscopy-assisted CT scan.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, frame 20 can be fabricated in a number of ways, from a number of different types of material, and may or may not be skeletal as is shown in the examples of FIGS. 1-6 of the present application. While a tripod arrangement of frame 20 has some advantages for stability, configurations using a different arrangement of extending members 24 could be utilized. A variety of techniques could be employed to adhere base 22 in position against the patient. Tabs could be provided, extending from base 22 to provide added skin contact area and to improve adhesion.

Thus, what is provided is an apparatus and method for stabilizing the position of a needle or other device inserted into a patient during medical testing or treatment.

PARTS LIST

10. Stabilizer
12. Needle
14. Entry point
18. Patient
20. Frame
22. Base
24. Extending members
26. Diaphragm
28. Aperture
30. Film
32. Pattern

The invention claimed is:

1. A stabilizing apparatus for stabilizing the position of a needle when penetrating the skin of a patient, the apparatus comprising:
    a) a frame structure having a base with a contact surface having an adhesive for adhesive placement against the skin in the vicinity of an intended needle entry point; and
    b) an unapertured flexible diaphragm supported by the frame structure and spaced apart from the base of the frame structure by a plurality of extending members that each extend from the base of the frame structure, to be disposed at a position away from the skin,
    wherein the flexible diaphragm is configured to releasably grip a shaft of the needle at a distance from the needle entry point.

2. The stabilizing apparatus of claim 1 wherein the flexible diaphragm is formed from an elastomer.

3. The stabilizing apparatus of claim 1 wherein a membrane with a visual grid pattern extends across the base of the frame structure.

4. The stabilizing apparatus of claim 1 wherein the frame structure and the flexible diaphragm are formed from the same material.

5. The stabilizing apparatus of claim 1 wherein the frame structure is skeletal to allow visibility of the needle entry point.

6. The stabilizing apparatus of claim 1 wherein the frame structure is formed from a plastic.

7. The stabilizing apparatus of claim 1 wherein the flexible diaphragm is formed from a rubber material.

8. The stabilizing apparatus of claim 6 wherein the plastic is an acrylic.

9. The stabilizing apparatus of claim 1 wherein the frame structure forms a tripod extending from the base to the flexible diaphragm.

10. The stabilizing apparatus of claim 1 wherein the needle entry point lies within an area bounded by the base.

11. A method for stabilizing the position of a puncturing instrument comprising:
    a) adhering a base portion of a frame structure to the skin of a patient in the vicinity of an intended entry point for the puncturing instrument;
    b) inserting the puncturing instrument through an unapertured flexible diaphragm supported by the frame structure at a distance spaced apart from the skin by a plurality of extending members that each extend from the base of the frame structure; and,
    c) penetrating the tip of the puncturing instrument beneath the skin of the patient at the entry point.

* * * * *